United States Patent [19]

Fulmer

[11] Patent Number: 4,875,912

[45] Date of Patent: Oct. 24, 1989

[54] SCENTED FURNACE FILTER

[76] Inventor: Thomas L. Fulmer, 800 E. Beau St., Apt. L2, Washington, Pa. 15301

[21] Appl. No.: 152,882

[22] Filed: Feb. 5, 1988

[51] Int. Cl.⁴ .............................................. A61L 9/04
[52] U.S. Cl. ........................................ 55/279; 239/56; 239/58; 422/123
[58] Field of Search .................... 55/279; 98/105, 109; 239/55, 56, 57, 58, 60; 422/120, 123, 124

[56] References Cited

U.S. PATENT DOCUMENTS

| | | | |
|---|---|---|---|
| 2,717,174 | 9/1955 | Casanovas | 239/56 |
| 2,757,957 | 8/1956 | Samann | 239/58 X |
| 3,065,915 | 11/1962 | Samann | 239/56 X |
| 4,028,073 | 6/1977 | Swain | 55/279 |
| 4,065,262 | 12/1977 | Petroff | 239/58 X |
| 4,145,001 | 3/1979 | Weyenberg et al. | 239/56 |
| 4,712,737 | 12/1987 | Hecking | 239/58 |

*Primary Examiner*—Harold Joyce
*Attorney, Agent, or Firm*—William J. Ruano

[57] ABSTRACT

A combination of a furnace filter and a scented evaporant packet inserted in a cut out portion of the filter. The evaporant is contained and wrapped in foil when not in use. Upon partial or entire removal of the foil by a tear tab, the evaporant is exposed to the air flowing in the cold air duct of a furnace—Such as used in dwellings, thereby the entire house may be scented. The secondary purpose of the evaporant is to give an indication of when the filter has to be replaced. This will occur when the scent is no longer evident in the air.

1 Claim, 1 Drawing Sheet

U.S. Patent    Oct. 24, 1989    4,875,912
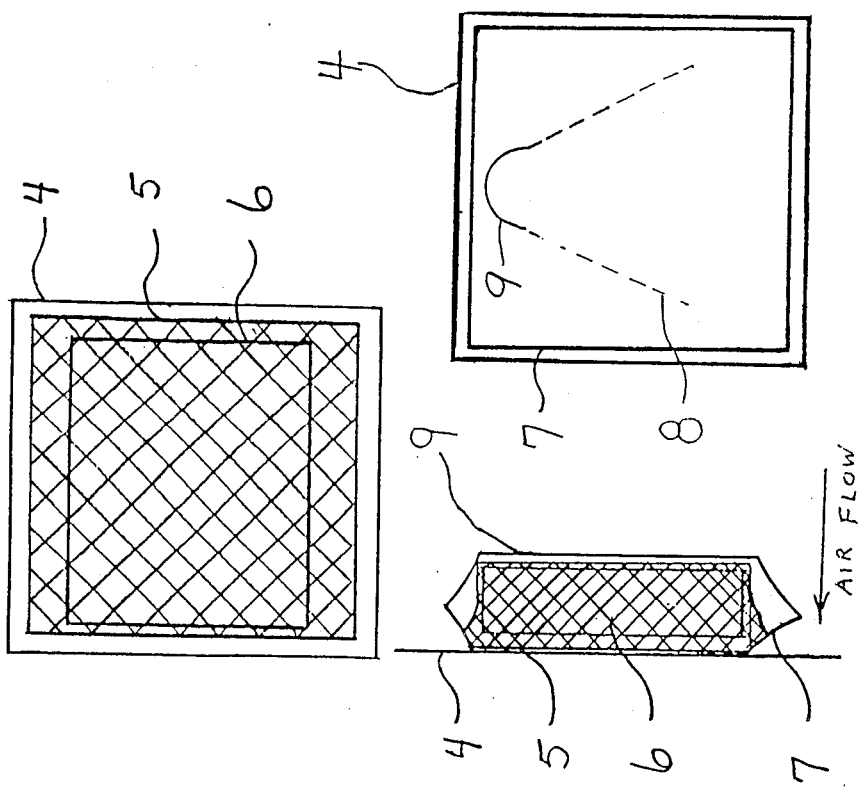
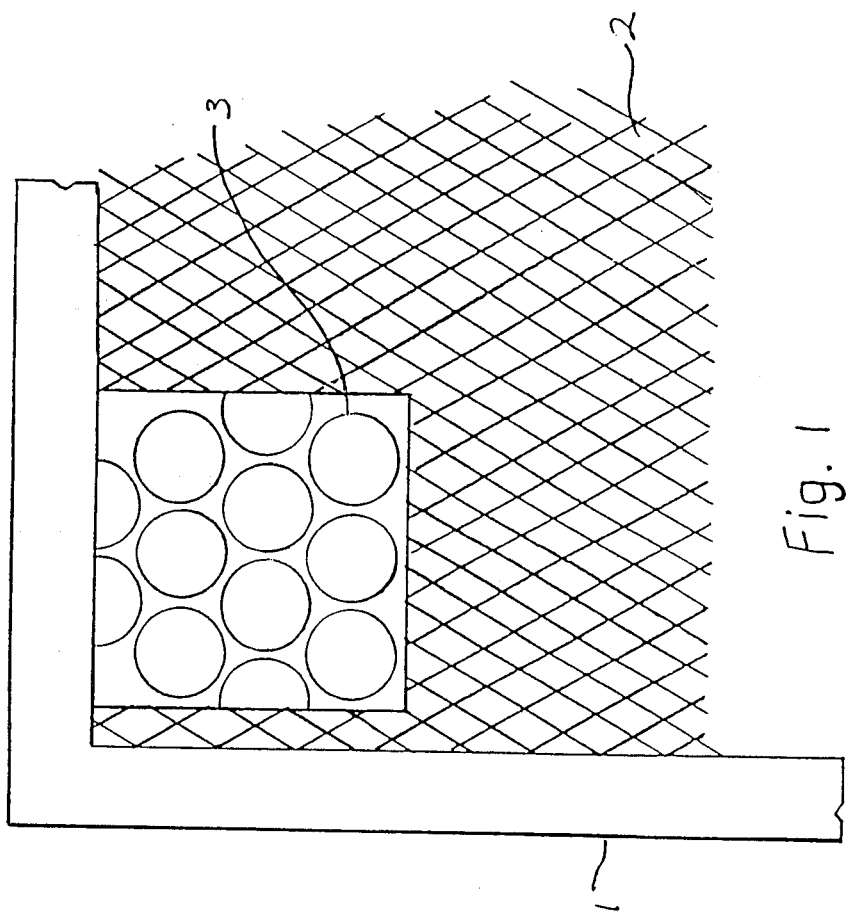

SCENTED FURNACE FILTER

This invention relates to a combination furnace filter and evaporant packet for the purpose of scenting all rooms of a dwelling.

BACKGROUND OF THE INVENTION

Air fresheners have been used in individual rooms, such as in combination with a grill, to which air is introduced into the room. A disadvantage of this arrangement is that it requires a separate packet and assembly in each room of the house to be scented. A further disadvantage is that it requires an expensive support.

SUMMARY OF THE INVENTION

An object of the present invention is to overcome these disadvantages by combining the evaporant packet with the main furnace filter whereby all the rooms may be simultaneously scented by a single packet.

A further object of the invention is to provide a scented detector for indicating, by the loss of scent, that the furnace filter needs replacing.

A still further object of the invention is to provide a novel scented packet which is normally sealed but which can be either partially or fully exposed to cold air flow by selectively tearing open either partially or entirely.

Other objects and advantages of the invention will become more apparent from a study of the following description taken with the accompanying drawing wherein:

BRIEF DESCRIPTION OF THE DRAWINGS

FIG. 1 is a fragmentary elevational view of a furnace filter having a cut-out portion for receiving a scented evaporant packet;

FIG. 2 is a plan view of the scented evaporant with its covering completely removed;

FIG. 3 is a vertical cross-sectional view of the packet shown in FIG. 2; and

FIG. 4 is an elevational view of the completely enclosed packet showing a pull tab for partially removing the packet cover.

DESCRIPTION OF THE PREFERRED EMBODIMENT

Referring more particularly to FIG. 1 of the drawing, numeral 1 denotes a furnace filter frame, generally of cardboard for receiving a filter 2 generally of matted fibre material. The filter 2 is reinforced by a perforated backing 3 which is visable in the upper left cut-out portion of the filter for receiving a scented evaporant packet of the construction shown in FIGS. 2, 3 and 4. Such backing may be of metal or plastic.

The scented evaporant packet fills the space of the cut-out portion of filter 2 and comprises a cardboard frame 4 having a peripheral portion surrounding the perimeter of the scented evaporant packet which includes a containment webbing 5 which completely encloses a scented wafer 6 of any desired scenting material and which has an outer covering 7 of metal foil or any other suitable material having perforations 8 terminating a pull tab 9.

In operation, the scented wafer 6 is completely sealed by the metal foil and outer covering 7, as shown in FIG. 4, so that the scenting material is not exposed to the surrounding air.

When the furnace filter 2 is installed in the furnace and when it is desired to expose the scenting material to the cold air flow of the furnace, one merely pulls the tab 9 either part way, or the entire way defined by perforations 8 to expose at least the front central portion of the scented wafer 6.

The fact that only a central portion of scented wafer 6 is exposed to the cold air flow allows a reserve area along the perimeter which by capillary action, as well as gravity, will gradually replenish the exposed area with scenting material so as to lengthen the life of the wafer and allowing for a more controlled release of the perfume oil or scenting material of wafer 6. The cold air flowing through the furnace otherwise causes a somewhat rapid dispersion of the scenting material.

If the entire area of wafer 6 is to be exposed, the perforations would be located on the perimeter of the scenting wafer.

It is easy to replace the packet with another of the same or different scenting material by merely pulling it out of the void space shown in FIG. 1. The packet has indefinite shelf life and more filtering area is present since the metal reinforcing 3 is only one side rather than both sides of the filter.

Thus it will be seen that I have provided a novel combination of a household filter having a cut-out portion for receiving a small packet of scenting material having a variable life of relatively long duration and means for selectively varying the extent of exposure of the scented material to the cold air flow, also which enables quick and easy replacement of the scenting packet.

While I have illustrated and described a single specific embodiment of my invention, it will be understood that this is by way of illustration only and that various changes and modifications may be contemplated in my invention within the scope of the following claims:

I claim:

1. In combination with a filter mounted in a frame for use in a household furnace for mounting in the cold air return of said furnace, a cut-out portion in said filter, a relatively small packet of scenting material inserted into and filling the entire area of said cut-out portion, said packet being sealed by a rear cover and a front cover for said scenting material having a substantially triangular tear tab for progressively exposing at least a portion of said scenting material to enable selective exposure of only the front portion of said scenting material, said tear tab being so located on said front cover as to expose only a portion of the scenting material, leaving uncovered a surrounding portion of the exposed area so that such surrounding portion serves as a reservoir for supplying scenting material to replace that which is discharged from said cut-out portion so as to lengthen the life of the scenting material.

* * * * *